United States Patent [19]

Laniado

[11] Patent Number: 5,398,688
[45] Date of Patent: Mar. 21, 1995

[54] METHOD, SYSTEM AND INSTRUMENT FOR MONITORING FOOD INTAKE

[75] Inventor: Shlomo Laniado, Tel Aviv, Israel

[73] Assignees: Aurora Dawn Ltd., Tel Aviv; Naftalie Stern, Nir Zvi; Arie Roth, Tel Aviv; Eliezar Bar-Nathan, Tel Aviv, all of Israel

[21] Appl. No.: 278,509

[22] Filed: Jul. 21, 1994

[51] Int. Cl.$^6$ .............................................. A61B 8/00
[52] U.S. Cl. ............................... 128/660.02; 128/690; 364/413.29
[58] Field of Search .............. 128/690, 670, 672, 677, 128/660.02, 661.07, 661.08; 364/413.29, 413.02, 413.03

[56] References Cited

U.S. PATENT DOCUMENTS

| | | | |
|---|---|---|---|
| 4,796,182 | 1/1989 | Duboff | 364/413.29 |
| 4,951,197 | 8/1990 | Mellinger | 364/413.02 |
| 5,243,992 | 9/1993 | Eckerle et al. | 128/690 |

*Primary Examiner*—George Manuel
*Attorney, Agent, or Firm*—Helfgott & Karas

[57] ABSTRACT

A method for monitoring food intake for an individual and providing an indication when the food intake exceeds a predetermined allowable amount, comprising the steps of monitoring the individual over a predetermined period of time in order to establish an empirical relationship for the individual between a change in at least one physiological variable and a rate and/or amount of food intake. Upon starting each meal, the change in each of the relevant physiological variables is measured so as to determine from the empirical relationship an estimated rate and/or amount of food intake. This permits calculation of a maximum eating time to intake the predetermined allowable amount for the individual, upon expiry of which an indication is given to stop eating. A system operating in accordance with the invention includes a wrist watch having a Doppler ultrasound transducer for placing over the user's radial artery and producing an audible alarm when the individual has been eating for sufficient time to consume the predetermined allowable amount of food. The watch can, if desired, also include a self-programming facility for allowing determination of the empirical relationship for the individual.

28 Claims, 8 Drawing Sheets

METHOD, SYSTEM AND INSTRUMENT FOR MONITORING FOOD INTAKE

FIELD OF THE INVENTION

This invention relates to a method and system for controlling dieting. In particular, it relates to a method, system and instrument for monitoring food intake of an individual.

BACKGROUND OF THE INVENTION

It is not an exaggeration to say that many hundreds of dieting techniques have been proposed based on different and varied principles, some sound and others not so sound and even damaging. The fundamental principle on which every sound method of dieting is based is that, in order to lose weight the caloric intake must be less than the energy output of the individual.

However, this relationship between the expenditure and the intake of energy is asymmetric and thus, for example, in order to expend the caloric intake added to the body consequent to eating a single slice of bread, it would be necessary for the individual to walk approximately one kilometer. The conclusion, therefore, is that increasing the energy expenditure, by means of exercise, is not itself sufficient to lose weight and that limiting the caloric intake by eating less is essential. This having been said, such a formula is problematic because the amount of food which is required is a function of appetite and even hunger of the individual.

What is required, therefore, is some way of controlling the mouth of the would-be dieter. Possibly the best form of control would be for the diet instructor to stand by the dieter for 24 hours a day and to warn him when he has eaten enough and to instruct him, at that point, to stop eating. Clearly, such an ideal solution is impractical. It would, however, clearly be desirable to propose an alternative method approximating such an approach.

SUMMARY OF THE INVENTION

It is an object of the invention to provide a method, system and instrument for monitoring food intake in which the drawbacks associated with hitherto proposed methods and systems are significantly reduced or eliminated.

According to one aspect of the invention there is provided a method for monitoring food intake for an individual and providing an indication when the food intake exceeds a predetermined allowable amount, the method comprising the steps of:

(a) monitoring the individual over a predetermined period of time in order to establish an empirical relationship for the individual between a change in at least one physiological variable and a rate and/or amount of food intake, (b) upon starting each meal, measuring the change in said at least one physiological variable and determining from said empirical relationship an estimated rate and/or amount of food intake and calculating therefrom a maximum eating time for the intake of said predetermined allowable amount, (c) measuring an elapsed time from the start of the meal, and (d) when the measured elapsed time is equal to or greater than the calculated maximum eating time, indicating to the individual to stop eating.

The invention is based on the various physiological changes and processes which occur in the body during eating. For example, along with the well known increases in the secretion of salivary juices and of various enzymes major alterations also take place in the cardiovascular system comprising the individual's heart and blood vessels. The most noticeable changes in the cardiovascular system during the process of eating are a rise in the heart rate and heart output and a lowering of the resistance of the peripheral blood vessels. As a result of experimentation, it has been found that the rise in the heart output is not dependent only on the rise in pulse rate, but also results from an increase in the heart stroke volume.

The changes in the cardiovascular system are a result of the processes which occur in the digestive system, circulation and nervous system during eating. The specific magnitude of the response and its nature depend on the caloric value of the meal and its constituents, i.e. food categories, proteins, fats and carbohydrates and speed of eating. The sensitivity of the reaction of the cardiovascular system is individual and varies greatly from one person to the next.

The invention provides a novel framework for dieting which, in accordance with one preferred embodiment, includes an institution or workshop for monitoring the various activities associated with the invention. Each prospective dieter is given a non-invasive medical examination in the institution in order to determine his specific cardiovascular reaction throughout three normal meals during the course of a day. The amount of food and its composition are varied during the different meals in order to provide as much information as possible on the various possible reactions of the prospective dieter under examination. This initial monitoring process is computerized and continues for a week or more in order to increase the statistical likelihood that the observed reactions are reliable and reproducible. Analysis of the results permits a fairly good prediction of the expected cardiovascular reaction during a meal, in respect of the specific individual under examination and, conversely, determination of the cardiovascular reaction permits assessment of the amount of food eaten during a meal. Furthermore, this is done without the appraiser being present during the eating process but, rather, is based only on the analysis of data which has already been recorded and stored in a microcomputer.

By another preferred embodiment the initial monitoring is performed by the prospective dieter himself by means of an instrument attached to his body that includes monitor means.

It will be clear that in order to derive a reliable correlation, each prospective dieter must exercise sufficient self-control and discipline, since different people are able to exhibit recognized variations in their body reactions to an identical meal. The initial monitoring is carried out over a period of approximately one to two weeks in order to ensure that, despite such variations which are influenced by different types of meal, meal times and so on, the average provides for a sufficiently accurate baseline to permit satisfactory control of the prospective dieter's eating habits.

BRIEF DESCRIPTION OF THE DRAWINGS

In order to understand the invention and to see how the same may be carried out in practice, a preferred embodiment will now be described, by way of non-limiting example only, with reference to the accompanying drawings, in which.

DETAILED DESCRIPTION OF PREFERRED EMBODIMENTS

Figure 1:
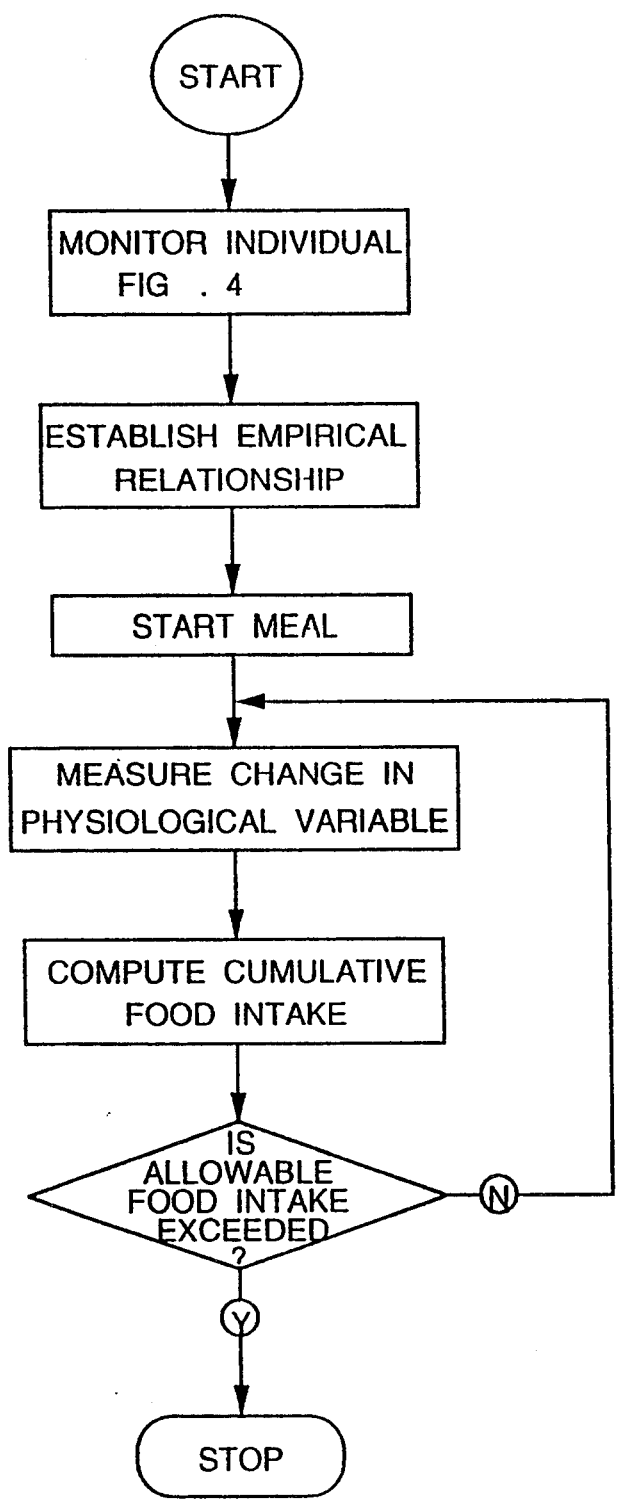
FIG. 1 is a flow diagram showing the principal steps in a method according to the invention.

FIG. 1 is a flow diagram showing the principal steps associated with a method according to the invention for monitoring the food intake of an individual. In the first stage, the individual is monitored in order to establish an empirical relationship for the individual between one or more physiological variables and an amount of food intake. The manner in which this is done will be described in more detail below, with particular reference to FIG. 4 of the drawings. At this stage, it is sufficient to understand that the empirical relationship permits a change in one or more physiological variable of the individual to be correlated with a rate and/or amount of food intake. Thus, by measuring the actual change in the physiological variables during eating after the empirical relationship has been established for the individual, the empirical relationship may then be employed in a reverse manner to estimate the rate and/or amount of food intake. This provides an indication of the maximum permitted time during which the individual may eat in order not to exceed his maximum allowable food intake.

It has been found that the physiological variables most susceptible to defined changes owing to food consumption are first, heart rate and second, stroke volume, i.e. the volume of blood pumped by the heart through the blood vessels per beat as determined by radial artery flow. However, it is to be noted that other physiological variables may also be used as a guide to the rate and/or amount of food intake. For example, as a person eats, his skin temperature may rise and the change in skin temperature can be measured using a thermistor. Likewise, there are measurable changes in blood pressure and these can be effectively measured by means of a suitable ultrasonic or electronic transducer, e.g. a Doppler ultrasound transducer.

Figure 2:
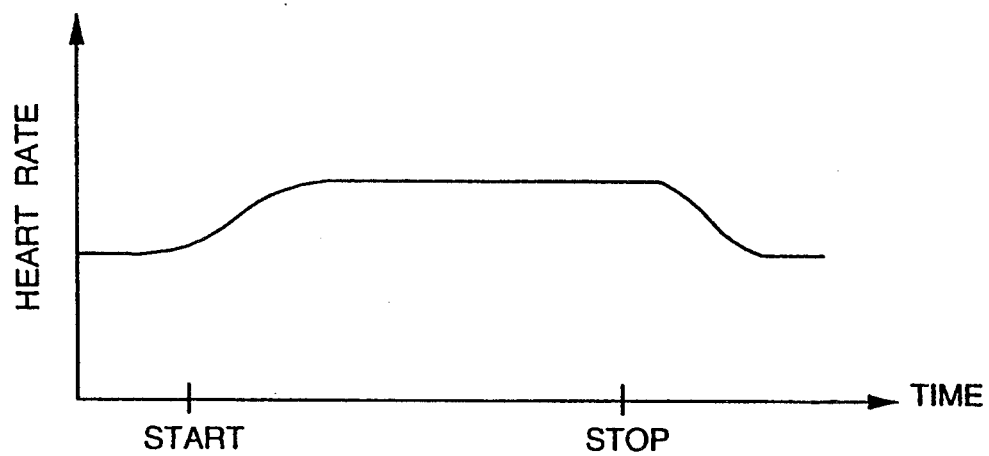
FIGS. 2 and 3 are graphical representations showing the effect of eating on heart rate and stroke volume.

FIG. 2 shows graphically the effect of eating on heart rate. It will be seen that when the individual starts eating, there is a rise in heart rate which settles down to a new, higher level during the course of the meal. After the individual stops eating, the heart rate falls to its original level. In fact, the heart rate may well start to rise even before the actual commencement of the meal, particularly if the individual is anxiously anticipating his meal for reasons of appetite, hunger, or for any other reason. Nevertheless, a difference still exists between the heart rate before and after eating, and the magnitude of this difference is related to the amount and rate of ingested food.

Figure 3:
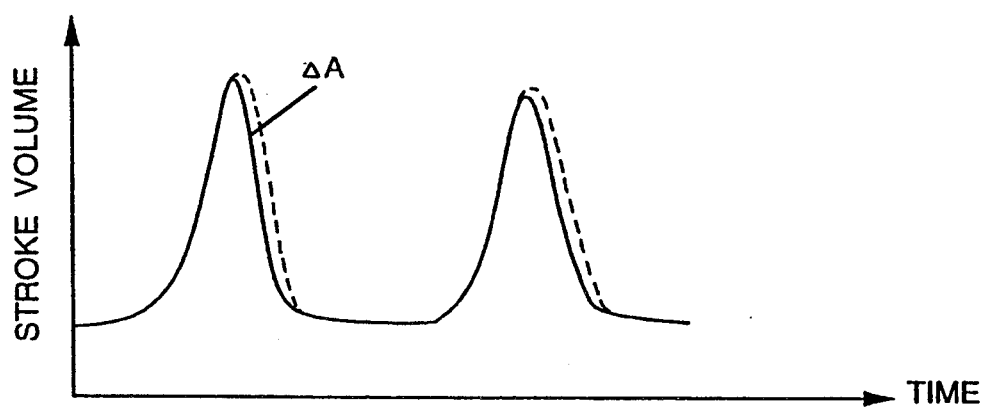

FIG. 3 shows graphically the effect of eating on the stroke volume curve. The general shape of FIG. 3 is equally applicable whether the pulse or blood flow rate is being measured, either of which can equally well be done with appropriate instrumentation. In either case, the area under the curve increases consequent to food intake and the differential area under the curve $\Delta A$ may be used as an empirical relationship for estimating the rate and/or amount of food intake and hence of overall food intake.

It should also be noted that in addition to the increase in heart rate and stroke volume, blood pressure also rises shortly after initiation of eating and so may be used as guide to determining an empirical relationship between change in blood pressure and food intake. Furthermore, regardless of which specific physiological variable or variables is/are employed for the formulation of the empirical relationship, the increments vary among individuals but are particularly related to caloric intake. Assuming a stable emotional status and roughly similar physical surroundings, time of day and food temperature, intra-individual variations in hemodynamic responses to food depend predominantly on caloric intake and rate of feeding. Thus, in the same individual, a large meal consumed swiftly elicits large increments in heart rate, stroke volume and blood pressure, whereas a small meal consumed casually over a long period of time, results in relatively minor changes. Thus, repetitive quantification of the hemodynamic responses in a given individual under basal ("pre-diet") conditions generates a reliable range of "dose response" patterns which may be utilized for subsequent programming aimed at caloric restriction and deceleration of feeding rate.

Figure 4:
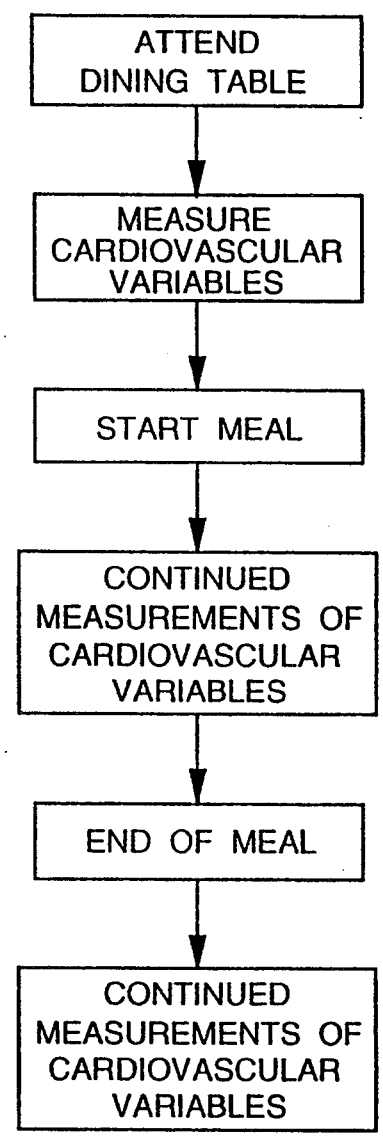
FIG. 4 is a flow diagram showing the principal steps associated with a monitoring phase of the invention.

Referring now to FIG. 4, there will be explained how the initial monitoring is performed in order to establish the empirical relationship between the change in the desired physiological variable and food intake. Prior to eating each meal, all of the above-mentioned cardiovascular variables are measured and recorded. Thereafter, the individual starts eating a pre-measured meal and any changes in the corresponding cardiovascular variables are measured and also recorded. In all respects, the prospective dieter eats at his normal pace and stops eating only when he has finished his meal. In other words, no pressure is put on the prospective dieter, at this stage, to eat less because the whole objective of the initial monitoring phase of the invention is to establish an empirical relationship between the measured cardiovascular variables and the specific individual's food intake under normal circumstances. The elapsed time during which the individual was eating is also measured and recorded and the whole cycle is repeated for as many meals as possible during the course of one week or as required, in a controlled environment.

Thus, during this week, constituting an initial monitoring phase, there will be recorded for each meal all respective changes in the monitored cardiovascular variables prior to the onset of eating and subsequent thereto. There will also be recorded the actual food intake for each meal. It is therefore a simple task to establish an average food intake for each of the meals eaten during the monitoring phase and a corresponding average change in the monitored cardiovascular variables.

This having been done, the standard deviation of the results is determined in order to establish whether the measured averages are sufficiently close to the sampled readings as to form a reliable baseline for future correlation of food intake from the change in the cardiovascular variables of interest.

It will be clear, in this regard, that the monitoring phase must be extended over a reasonable period of time in order to establish a reliable baseline. For example, if during the monitoring phase the individual eats only vegetarian meals whilst, under normal circumstances, he eats meat at least one meal a day, then the results will be skewed and will not provide a good basis for subsequent weight loss. Therefore, the initial monitoring phase is performed over a period of at least one week in order to establish a stable a reliable baseline. During this period, the repeat measurements allow the determination of the "best-fitting cardiovascular variable", i.e. the variable which is best related to the particular individual's food intake.

Figure 5A:
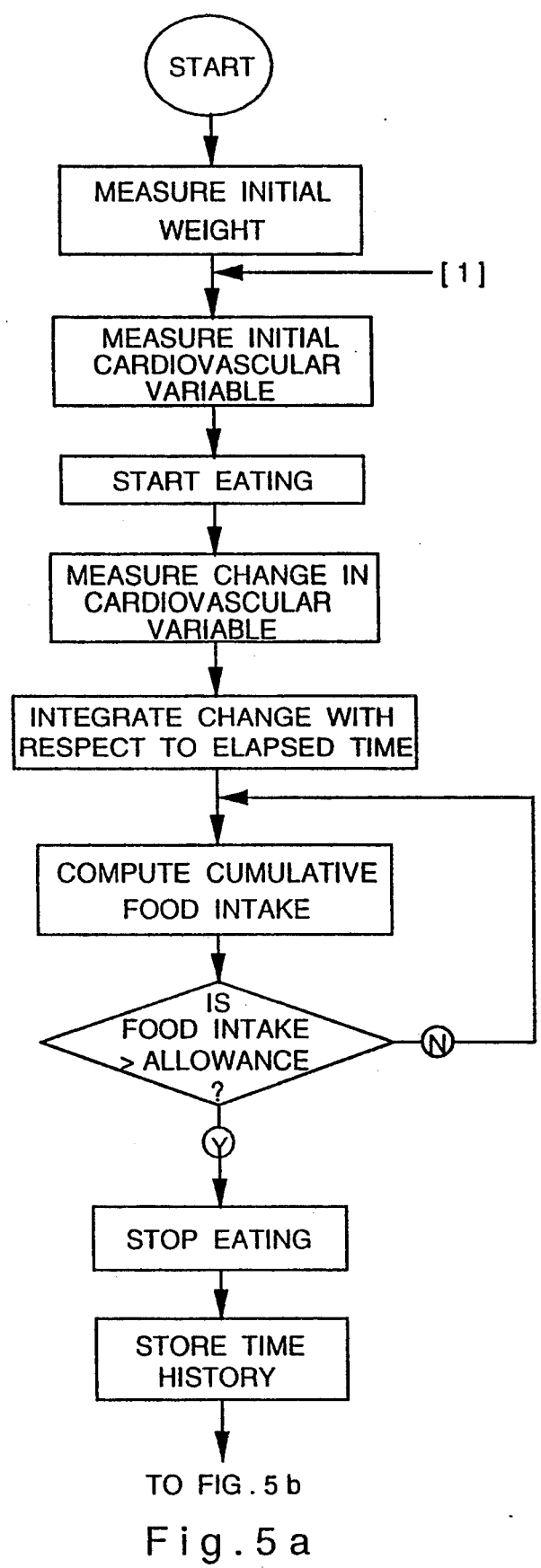
FIGS. 5a, 5b and 5c are flow diagrams showing the principal steps associated with a subsequent phase of the invention.
Figure 5B:
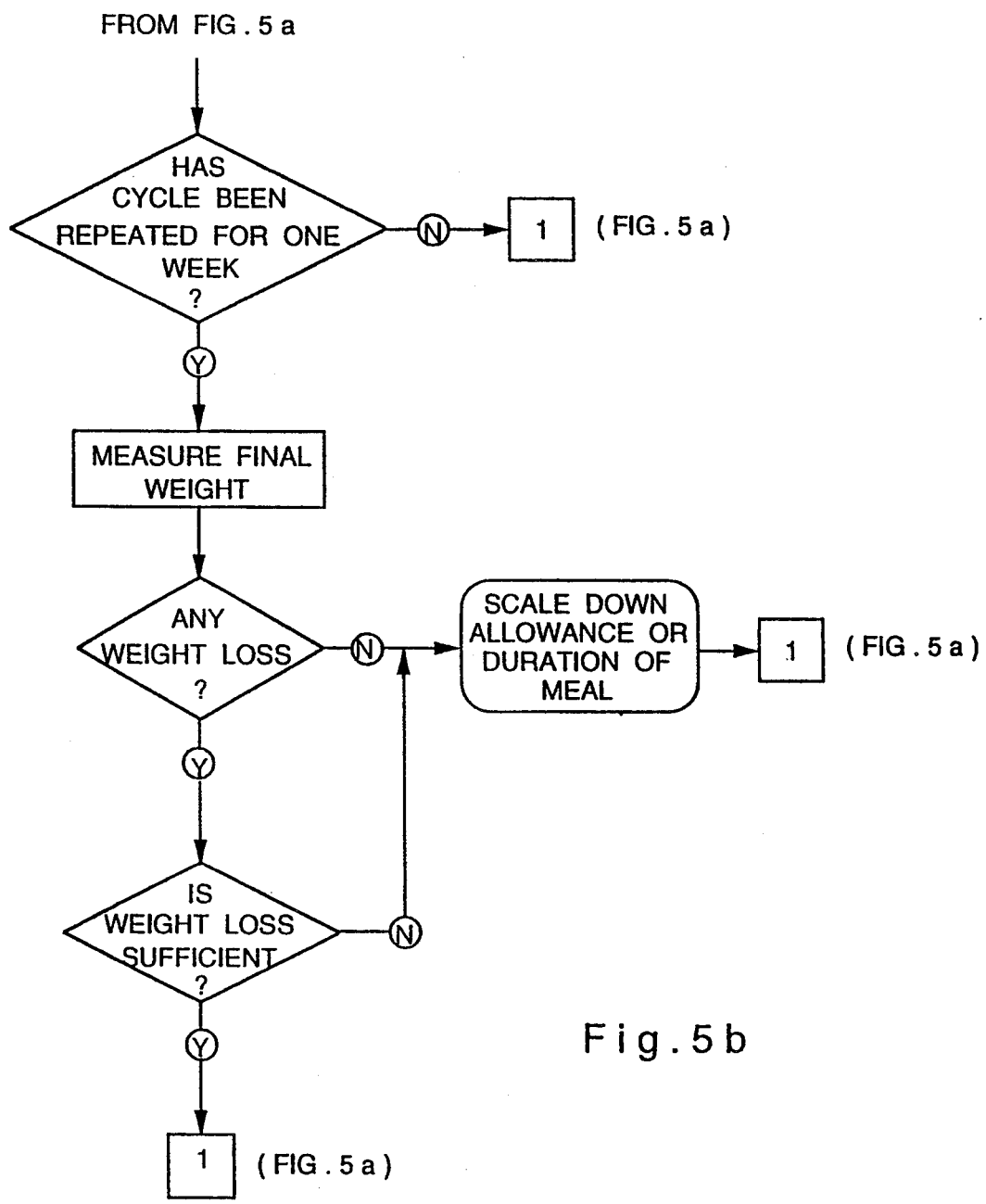

Referring now to FIGS. 5a, 5b of the drawings, there will be described a subsequent phase wherein the information derived during the initial monitoring phase is utilized to control food intake. Thus, at the outset, the individual's weight is measured and recorded at a specific, known time of day. Thereafter, the individual is allowed to eat freely for one additional week in his natural environment. The following week, at the same time as the individual's initial weight was measured, his weight is again measured and compared with the initial reading. If there is no measured weight loss, then it is clear that the same eating pattern cannot be allowed to prevail indefinitely if a weight loss is to be achieved. Therefore, in this case, the best fitting cardiovascular variable or the time duration of subsequent meals is curtailed relative to the measured and recorded parameters for the same meals previously. This will ensure that, providing in all other respects the same eating pattern is maintained, less food will be consumed and this is repeated, as required, until a weight loss is finally recorded. If the measured weight loss is insufficient, then the entire cycle of subsequent meals eaten during the course of a week is still further modified until the measured weight loss is acceptable.

Figure 5C:
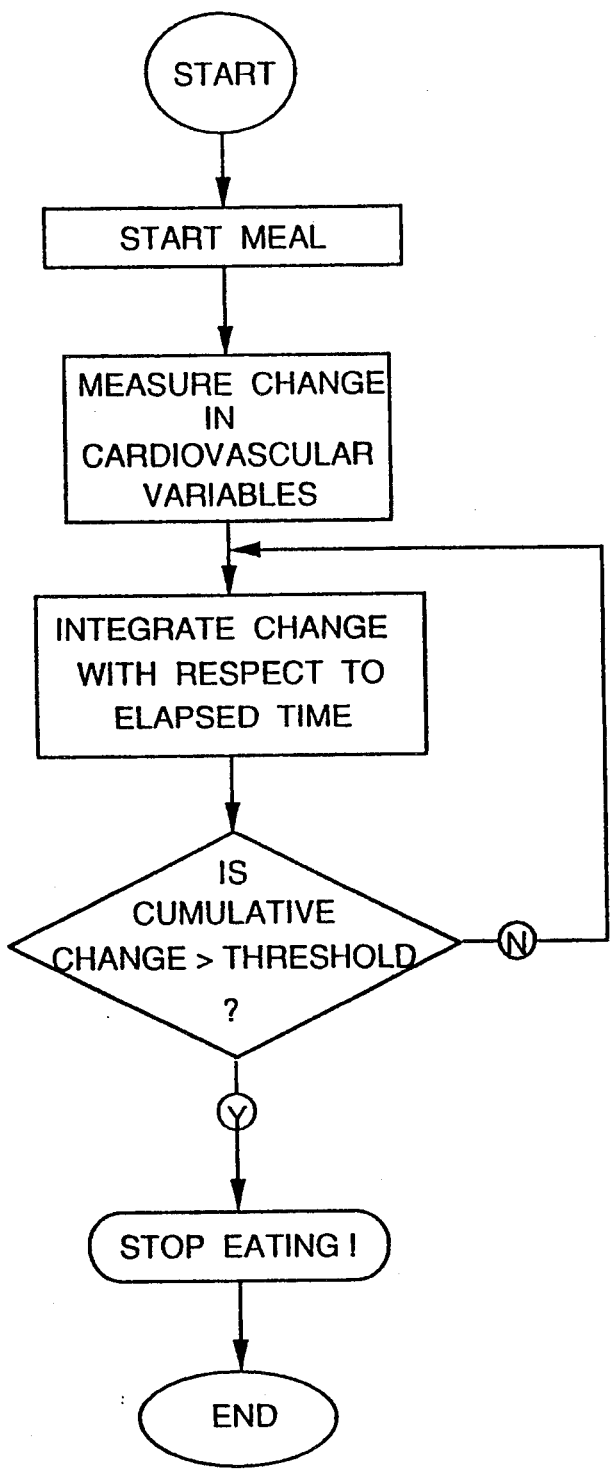

It will be understood that essentially the same steps shown in FIG. 5c are also employed during the subsequent phase of the method, i.e. during the actual process of eating wherein the initial monitoring phase is integrated into a feedback system. Thus, any changes in the appropriate cardiovascular variables are measured consequent to the onset of eating and the elapsed time also is measured from the moment the individual starts his meal. From a knowledge of the measured change in the cardiovascular variable or variables and also the empirical relationship between the change in cardiovascular variable and food intake, the estimated food intake may now be calculated. This then gives a measure of an integrated allowed response which determines for how long the individual may continue eating until the cumulative food intake exceeds the maximum allowed. This time interval having been calculated, as soon as the elapsed time during which the individual has been eating equals (or exceeds) the calculated value, an indication is given to the individual to stop eating.

Figure 6:
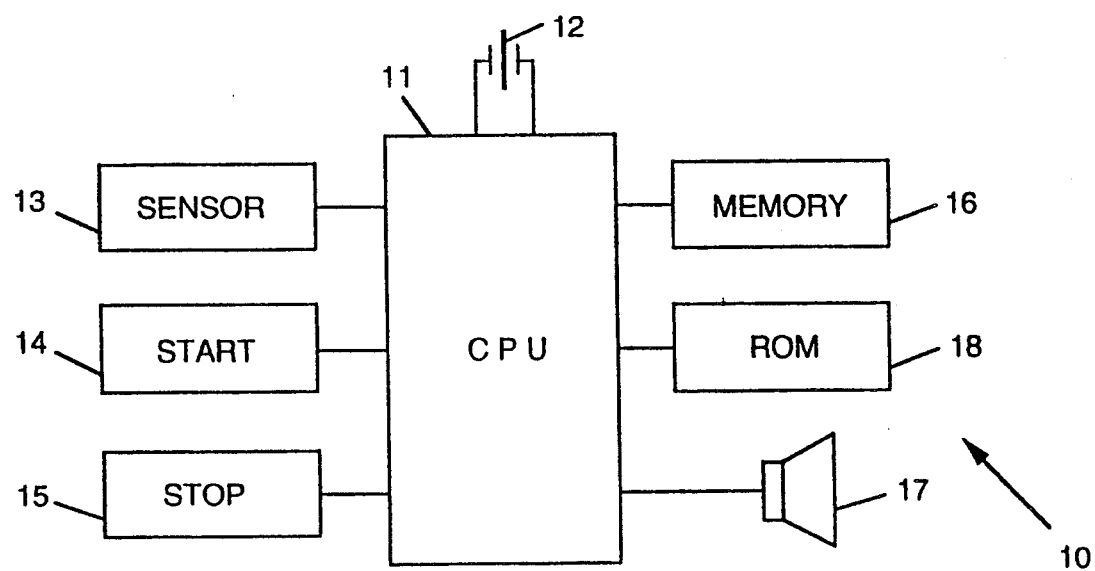
FIG. 6 is a block diagram showing the principal components in a monitoring instrument for carrying out the method shown in FIG. 4.

FIG. 6 shows functionally the principal components in an instrument depicted generally as 10 for carrying out the second phase of the method described above with reference to FIGS. 5a, 5b and 5c of the drawings. Thus, the instrument 10 includes a central processing unit (CPU) 11 operating at a predetermined clock frequency derived by means of a quartz crystal 12. Coupled to the CPU 11 is a sensor 13 which is preferably a Doppler ultrasound transducer which is located on the individual's radial artery for sensing the individual's heart rate or stroke volume. START and STOP switches 14 and 15, respectively, are coupled to the CPU 11 for indicating the start and stop times, respectively, of a meal eaten by the individual. Also connected to the CPU 11 is a memory 16 for storing therein a time history of cardiovascular variables measured by the sensor 13 whereby, after extended use of the instrument 10, the average, steady-state values of the cardiovascular variables prior to the onset of eating may be determined by reading time history from the memory 16 even without measuring the cardiovascular variable discretely prior to the onset of eating. This, of course, also overcomes any tendency to increased cardiovascular activity even prior to eating owing to anxiousness, hunger, appetite and so on. A small loudspeaker 17 is coupled to the CPU 11 and constitutes an indication means for indicating to the individual when to stop eating.

Preferably, the instrument 10 is in the form of a wristwatch and actually includes conventional watch functions so that, when the instrument 10 is not being used for the purpose of monitoring food intake, it can be used as a normal wristwatch. In use, the individual straps the instrument 10 to his wrist so that the sensor 13 overlies the radial artery and, at least until such time that a reliable time history of cardiovascular variables is stored in the memory 16, the pre-meal value is recorded and stored in the memory 16. This is not done discretely but, rather, is done under program control as soon as the instrument is switched on, the program being stored in a read only memory (ROM) 18 coupled to the CPU 11. This having been done, at the start of a meal, the START switch 14 is pressed whereupon the CPU 11 under program control starts to measure the elapsed time. Similarly, it calculates any difference in the cardiovascular variable sensed by the sensor 13 and by correlating the measured change with the empirical relationship already determined and stored in the ROM 18, the actual rate and/or amount of food intake is computed. A maximum allowable food intake is also stored in the memory 16 and by dividing this value by the calculated rate and/or amount of food intake, the maximum allowable eating time may likewise be computed. When this time has elapsed, the loudspeaker gives an audible indication signal under control of the CPU 11.

Figure 7:
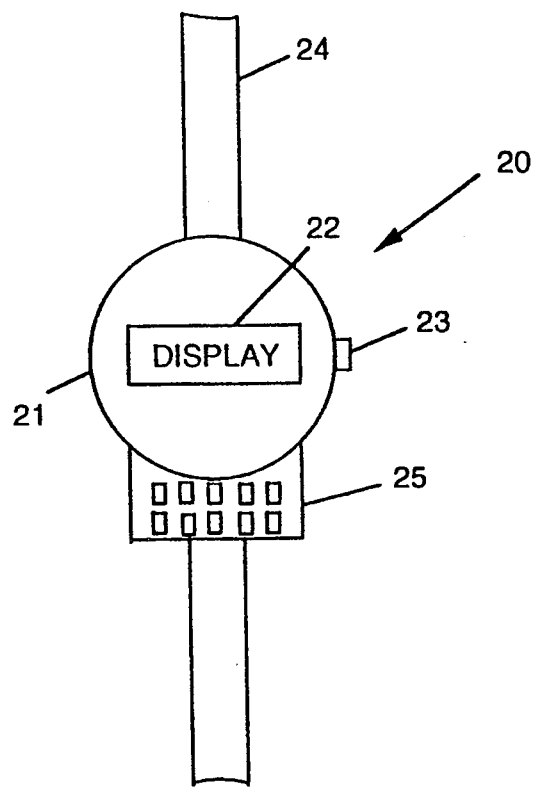
FIG. 7 is a pictorial representation of an integrated monitoring instrument for carrying out the method of FIGS. 4 and 5.

FIG. 7 shows pictorially a wristwatch 20 having a dial 21, a display window 22, a MODE switch 23 and a strap 24 for attaching the wristwatch 22 to the individual's wrist and itself constituting a sensor for overlying the radial artery so as to detect the required cardiovascular variable or variables. Thus far, the wristwatch 20 will fulfill the functions described above with reference to FIG. 6, it being assumed that the actual monitoring phase described above with reference to FIG. 4 of the drawings has already been performed and that the empirical relationship thus determined in pre-programmed into the ROM 18 or the memory 16 shown in FIG. 6.

However, the wristwatch 20 shown in FIG. 7 also includes a keyboard 25 for allowing the initial monitoring phase shown in FIG. 4 of the drawings to be performed by the prospective dieter himself, thereby obviating the need for him to attend an institution or workshop for several days or more prior to undertaking a diet, and the need for further attendance thereafter on regular basis.

The monitoring phase may be performed with the wristwatch 20 by pressing the MODE switch 23 a required number of times so that, under program control, a weight-entry mode is established whereupon the initial weight of the individual may be entered via the keyboard 25. When the individual starts to eat, the MODE switch 23 is set to an eating mode of operation, whereby depressing the MODE switch 23 once more starts the process shown in FIG. 4 and commences time measurement. At the end of the meal, pressing the MODE switch 23 a second time, indicates the end of the meal and terminates time measurement. The various sensor readings and calculations as well as the recorded weight are stored in the memory 16 and the whole cycle is repeated exactly as explained above with reference to FIGS. 5a and 5b until a suitably reliable baseline is determined.

Figure 8:
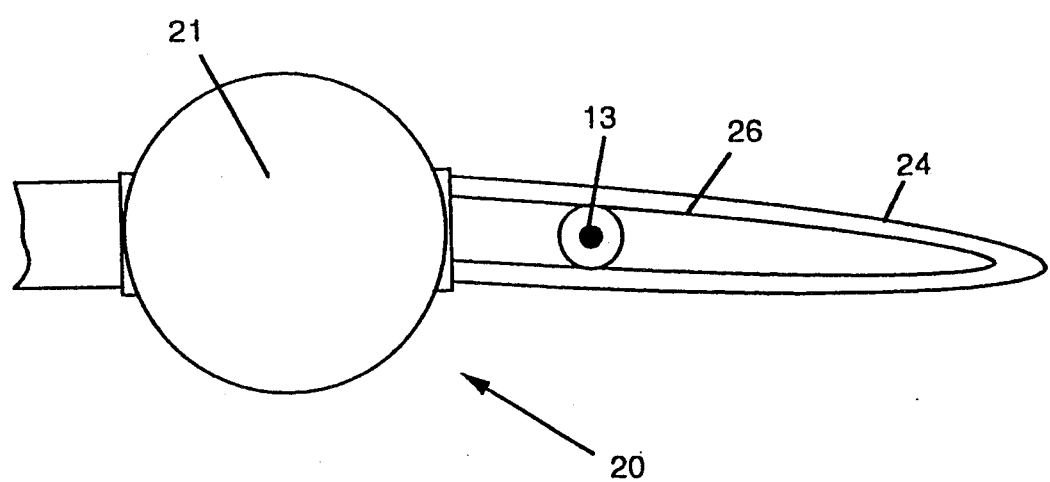
FIG. 8 is a pictorial representation of relating to a detail of the instrument shown in FIG. 7.

FIG. 8 shows pictorially a detail of a reverse view of the instrument 10 from which it will be seen that the strap 24 is provided on its lower surface with a peripheral track 26. The sensor 13 is slidably fixed to the strap 24 so as to allow movement of the sensor 13 within the peripheral track 26. During use, prior to attaching the instrument 20 to the individual's wrist, the dial 21 is positioned and the sensor 13 is moved around the individual's wrist relative to the dial 21 so as to allow positioning of the sensor 13 in proximity of the individual's radial artery.

It should be noted that whether the initial monitoring phase is done locally by the individual or, alternatively, whether it is done at a diet workshop or institution, the initial monitoring phase is checked after a period of two weeks by measuring the individual's weight in order to establish what weight loss, if any, has occurred over the two-week trial period. In the event that the initial monitoring phase is performed by an institution, the instrument is temporarily taken away from the individual and all of the values stored in the memory thereof, corresponding to the time history of the changes in the measured cardiovascular variables, are read and compared with the baseline values for the same individual. Processing the information thus obtained, including the weight loss and the recorded time histories, permits a more accurate estimation to be determined of the diet program and, if necessary, permits fine tuning to be effected to the program stored in the memory of the instrument. By this means the subsequent phase of the instrument, providing an indication to the individual when to stop eating, will be even more accurate in the future thereby reducing even more the actual quantity of food intake.

I claim:

1. A method for monitoring food intake for an individual and providing an indication when the food intake exceeds a predetermined allowable amount, the method comprising the steps of:
   (a) monitoring the individual over a predetermined period of time in order to establish an empirical relationship for the individual between a change in at least one physiological variable and a rate and/or amount of food intake,
   (b) upon starting each meal, measuring the change in said at least one physiological variable and determining from said empirical relationship an estimated rate and/or amount of food intake and calculating therefrom a maximum eating time for the intake of said predetermined allowable amount,
   (c) measuring an elapsed time from the start of the meal, and
   (d) when the measured elapsed time is equal to or greater than the calculated maximum eating time, indicating to the individual to stop eating.

2. The method according to claim 1, wherein the at least one physiological variable is a cardiovascular change.

3. The method according to claim 2, wherein the at least one physiological variable includes heart rate.

4. The method according to claim 2, wherein the at least one physiological variable includes stroke volume.

5. The method according to claim 2, wherein the cardiovascular change is measured by means of a transducer being a member of the group consisting of ultrasonic and electronic transducers located on the individual's radial artery.

6. The method according to claim 5, wherein the cardiovascular change is measured by means of a Doppler ultrasound transducer.

7. The method according to claim 1, further including the steps of:
   recording an initial weight of the individual,
   recording throughout a predetermined time interval each measurement of said at least one physiological variable,
   measuring a current weight of the individual at an end of said predetermined time interval, and
   comparing the initial weight with the current weight and correlating any weight loss with the recorded measurements of said at least one physiological variable in order to adjust said empirical relationship, as required.

8. The method according to claim 1, wherein said empirical relationship is programmed into a microcomputer operated by the individual.

9. A system for monitoring food intake for an individual and providing an indication when the food intake exceeds a predetermined allowable amount, said system comprising:
   monitoring means for monitoring the individual over a predetermined period of time in order to establish an empirical relationship for the individual between a change in at least one physiological variable and a rate and/or amount of food intake,
   measuring means for attaching to the individual and for measuring said at least one physiological variable during a meal,
   computing means coupled to the measuring means for computing a change in said at least one physiological variable and, in accordance with said empirical relationship, computing an estimated rate and/or amount of food intake and a maximum eating time to intake said predetermined allowable amount,
   timing means for measuring an elapsed time from commencement of the meal,
   comparing means coupled to the timing means for producing an indication signal when the measured elapsed time exceeds the computed maximum eating time, and
   indication means coupled to the comparing means and responsive to the indication signal for indicating to the individual to stop eating.

10. The system according to claim 9, wherein the monitoring means is adapted to be located at a diet laboratory.

11. The system according to claim 9, wherein the at least one physiological variable is a cardiovascular change.

12. The system according to claim 11, wherein the measuring means is a transducer being a member selected from the group of ultrasonic and electronic transducers attached to a radial artery of the individual.

13. The system according to claim 12, wherein the measuring means is a Doppler ultrasonic transducer.

14. The system according to claim 11, wherein the cardiovascular change includes heart rate.

15. The system according to claim 11, wherein the cardiovascular change includes stroke volume.

16. The system according to claim 9, wherein the computer means is a microcomputer adapted to be carried by the individual.

17. The system according to claim 16, wherein the microcomputer is provided with start and stop means for indicating a start and stop, respectively, of a meal.

18. The system according to claim 9, wherein the indication signal is audible.

19. The system according to claim 9, wherein the measuring means, the computing means, the comparing means and the indication means are all integrated in a single instrument.

20. The system according to claim 19, wherein the instrument is adapted to be worn by the individual.

21. The system according to claim 20, wherein the instrument is adapted to be worn on the individual's wrist with the measuring means located to proximate the individual's radial artery.

22. For use with the system according to claim 9, an instrument for indicating to an individual who wishes to change weight when to stop eating, the instrument comprising:
memory means for storing therein an empirical relationship for the individual between a change in at least one physiological variable and a rate and/or amount of food intake,
measuring means for measuring said at least one physiological variable during a meal,
computing means coupled to the measuring means and to the memory means for computing a change in said at least one physiological variable and, in accordance with said empirical relationship, computing an estimated rate and/or amount of food intake and a maximum eating time to intake said predetermined allowable amount,
timing means for measuring an elapsed time from commencement of the meal,
comparing means coupled to the timing means for producing an indication signal when the measured elapsed time exceeds the computed maximum eating time, and
indication means coupled to the comparing means and responsive to the indication signal for indicating to the individual to stop eating.

23. The instrument according to claim 22, further including an attaching means for attaching the instrument to the individual.

24. The instrument according to claim 23, being generally in the form a wristwatch and wherein the attaching means is a strap for attaching to the individual's wrist.

25. The instrument according to claim 24, wherein:
there is provided a display means coupled to the strap for displaying time, and
the measuring means is slidably fixed to said strap so as to allow movement of the measuring means around the individual's wrist relative to said display means;
thereby allowing the individual to locate both the display means and the measuring means at independently variable positions.

26. The instrument according to claim 25, wherein the measuring means is a Doppler ultrasound transducer.

27. The instrument according to claim 22, further comprising a coupling means connected to the memory means for coupling to an external device for downloading the empirical relationship into said memory means.

28. The instrument according to claim 22, further including:
an input means coupled to the memory means for entering a weight of the individual for storage in the memory means, and
self-programming means coupled to the memory means and responsive to a time history of changes in said at least one physiological variable produced during a plurality of meals, to a corresponding time history of elapsed meal times, to a corresponding time history of quantities of food intake and to a time history of weights taken over an extended period of time, all of said time histories being stored in the memory means, for computing said empirical relationship and storing it in the memory means.

* * * * *